United States Patent [19]

Goble et al.

[11] Patent Number: 5,451,224

[45] Date of Patent: Sep. 19, 1995

[54] APPARATUS FOR RADIO FREQUENCY BIPOLAR ELECTROSURGERY

[75] Inventors: Nigel M. Goble, Nr. Cardiff; Colin C. O. Goble, Cardiff, both of United Kingdom

[73] Assignee: G2 Design Limited, United Kingdom

[21] Appl. No.: 23,191

[22] Filed: Feb. 25, 1993

[30] Foreign Application Priority Data

Feb. 27, 1992 [GB] United Kingdom ................. 9204218

[51] Int. Cl.⁶ ............................................. A61B 17/39
[52] U.S. Cl. ........................................ 606/48; 606/50; 606/51; 219/233; 219/236
[58] Field of Search ..................... 606/28–31, 606/34, 37–40, 41, 45–52; 219/229, 230, 233, 236–239

[56] References Cited

U.S. PATENT DOCUMENTS

| Re. 31,723 | 11/1984 | Shaw | 128/303.1 |
|---|---|---|---|
| 3,768,482 | 10/1973 | Shaw | 606/29 |
| 4,089,336 | 5/1978 | Cage et al. | 606/31 |
| 4,219,025 | 8/1980 | Johnson | 128/303.1 |
| 4,231,371 | 11/1980 | Lipp | 600/31 |
| 4,359,052 | 11/1982 | Staub | 128/330.1 |
| 4,691,703 | 9/1987 | Auth et al. | 128/303.1 |
| 4,850,353 | 7/1989 | Stasz et al. | 128/303.14 |
| 4,958,539 | 9/1990 | Stasz et al. | 76/104.1 |

FOREIGN PATENT DOCUMENTS

| 2647683 | 3/1990 | France . | |
|---|---|---|---|
| 75343 | 3/1893 | Germany . | |
| 2452695 | 5/1976 | Germany | 606/28 |
| 3707820A1 | 9/1987 | Germany . | |
| 384134 | 1/1965 | Switzerland . | |
| 2214430 | 9/1989 | United Kingdom . | |

*Primary Examiner*—Lee S. Cohen
*Attorney, Agent, or Firm*—Fish & Richardson

[57] ABSTRACT

Surgical apparatus for bipolar diathermy has a radio frequency generator connectible to a cutting assembly which includes a support structure having a pair of electrical supply conductors and, mounted at the distal end of the support assembly, a tissue cutting head. The cutting head comprises a loop of material which is electrically conducting and has a negative temperature coefficient (NTC) of resistance, such as silicon carbide. In operation, radio frequency power from the generator causes heating of the loop to a temperature at which its resistivity rises to level which exceeds that of living tissue with the result that diathermy currents pass through the tissue. Also disclosed is a pair of forceps with electrodes made of NTC material, for cauterization.

14 Claims, 5 Drawing Sheets

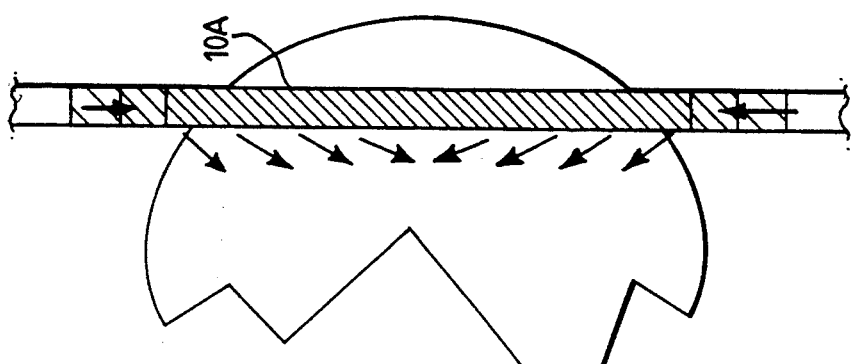
Fig.1D.
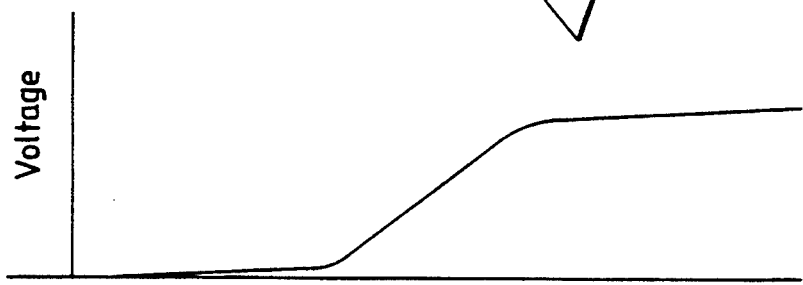
Fig.1C.
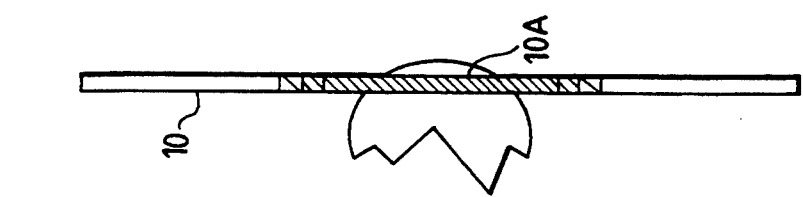
Fig.1B.
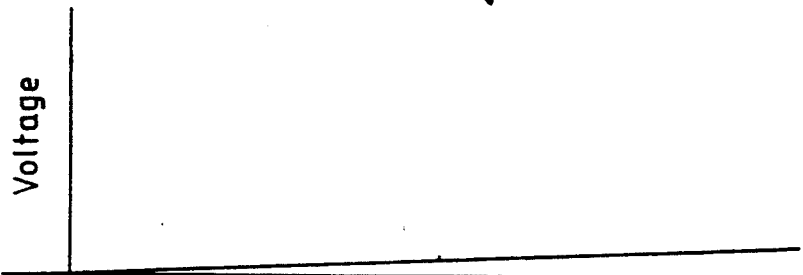
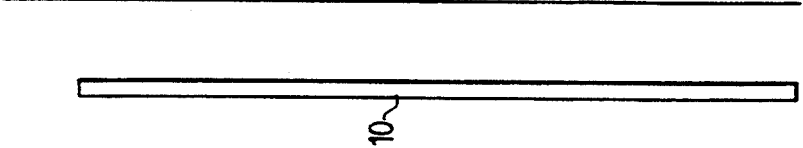
Fig.1A.
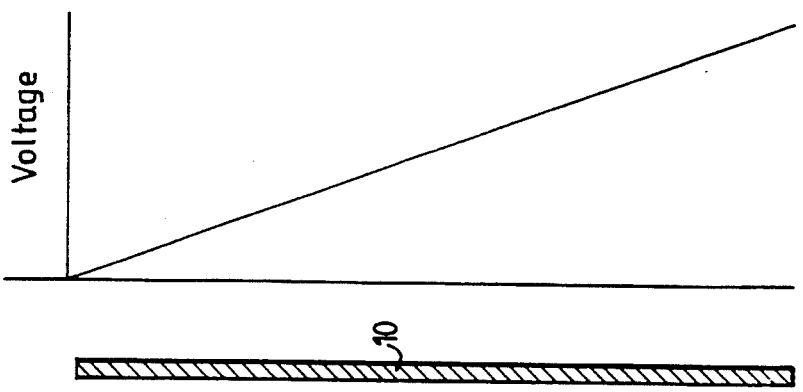

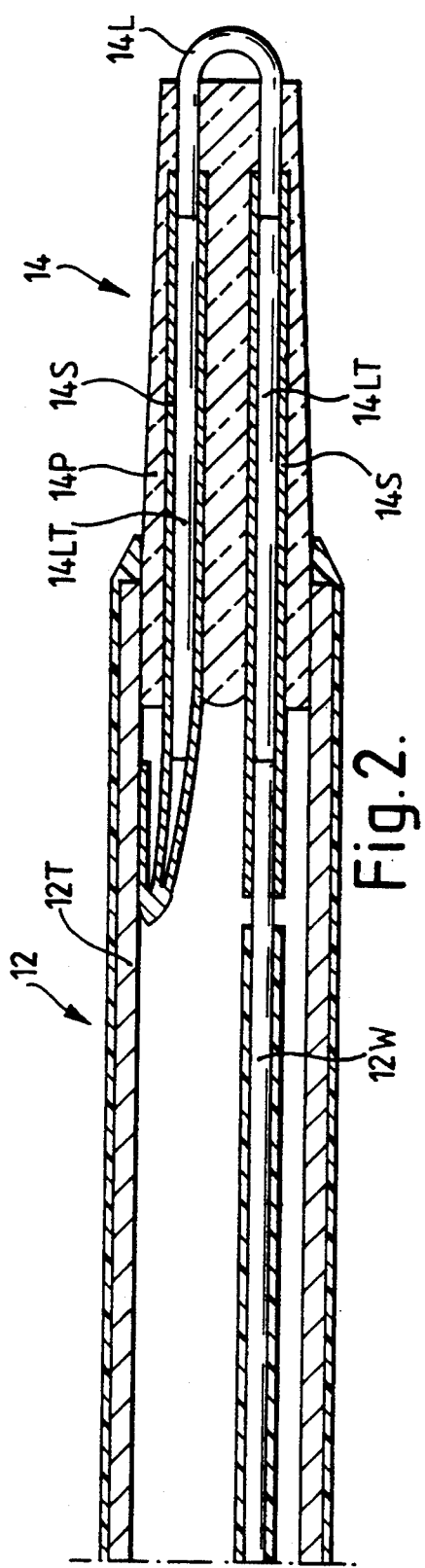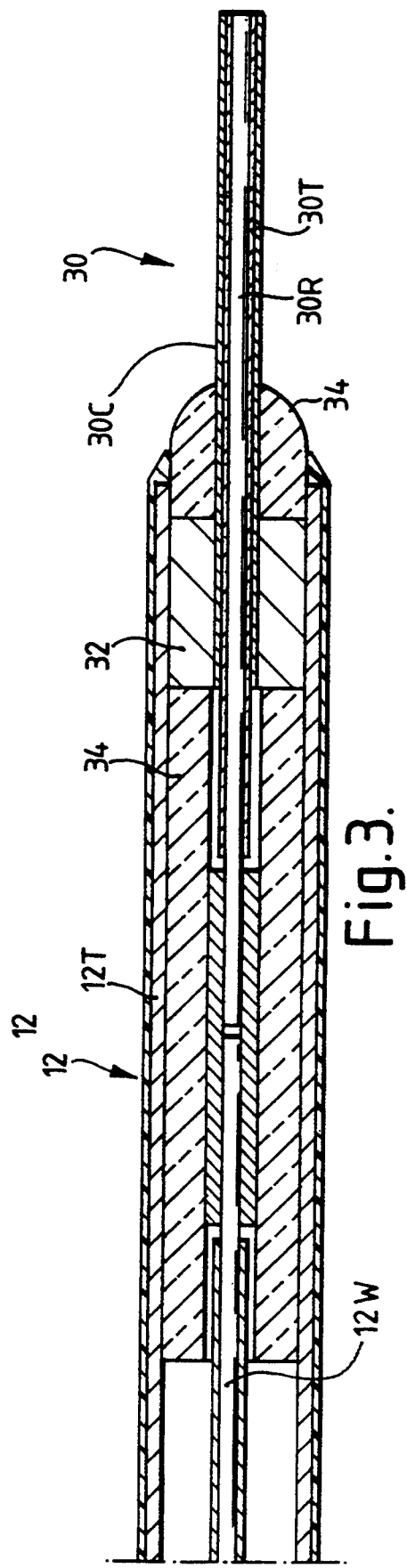

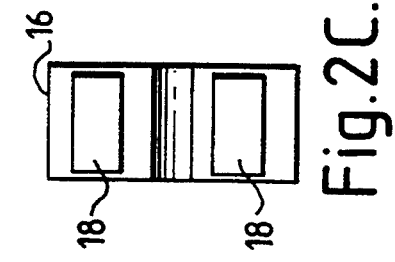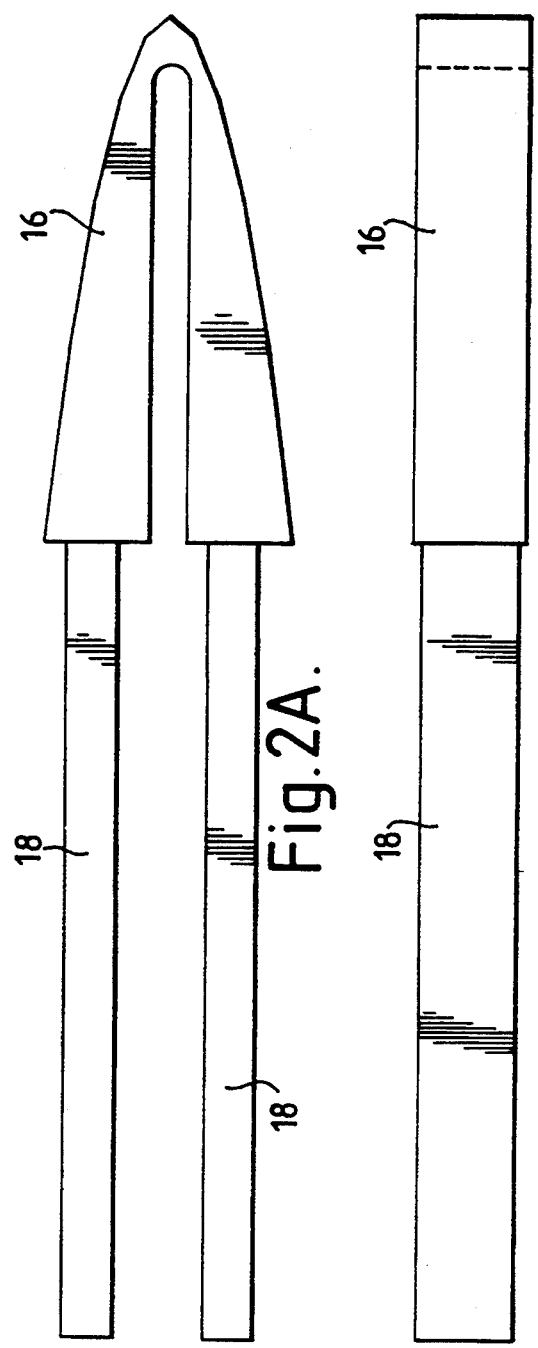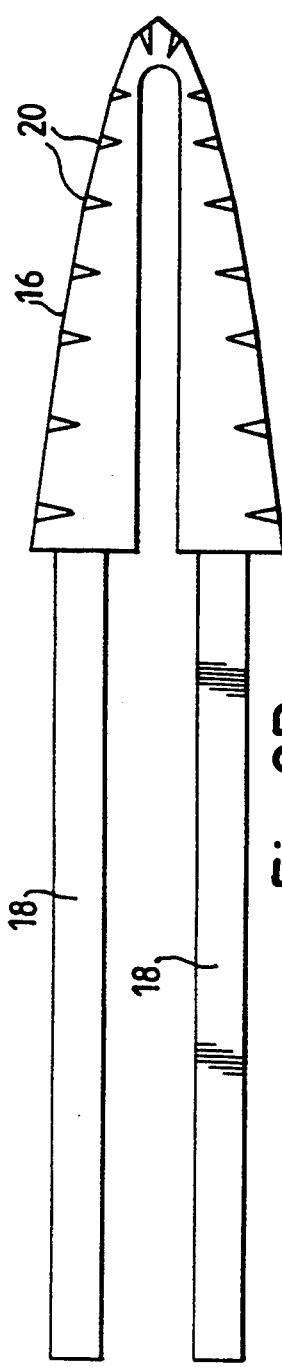

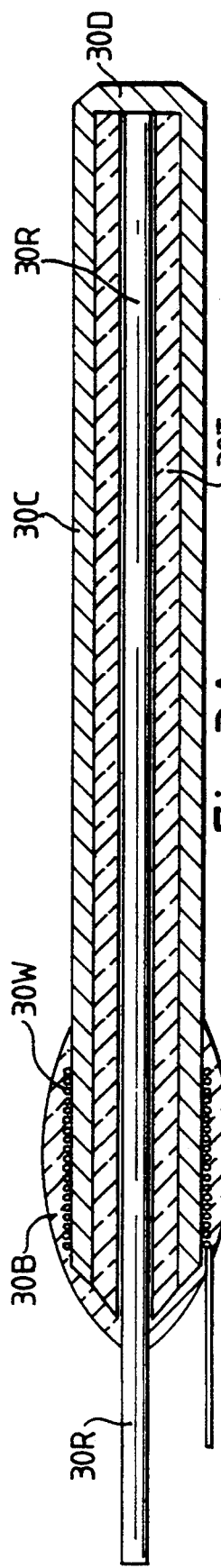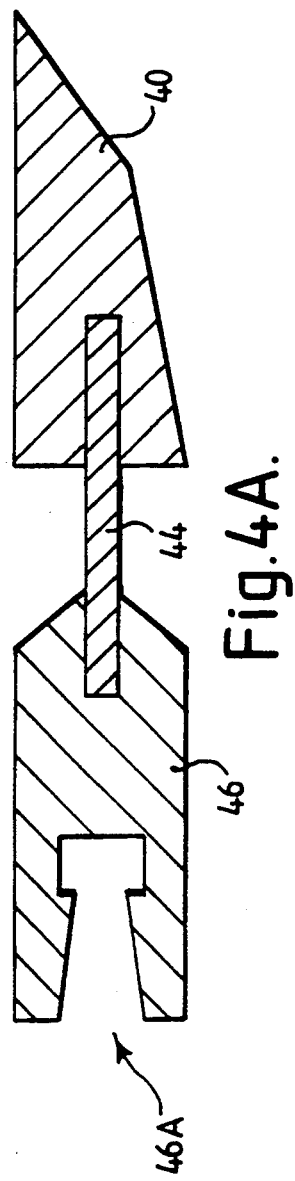
Fig.3A.
Fig.4.
Fig.4A.

APPARATUS FOR RADIO FREQUENCY BIPOLAR ELECTROSURGERY

BACKGROUND OF THE INVENTION

This invention relates to a apparatus for bipolar electrosurgery, and in particular to surgical apparatus and a cutting assembly for cutting living tissue using the principle of radio frequency (RF) electrosurgery.

Bipolar RF electrosurgery historically has only been used for coagulation. Cutting by RF electrosurgery is normally performed by monopolar devices. The difference between the two techniques is that a bipolar device has two active electrodes for use at the site of operation, whereas a monopolar device has a fixed return electrode (usually a plate positioned on the patient's thigh or back) and one active electrode.

The established means for providing electrosurgical cutting is by producing very high voltage levels, typically in excess of 300 volts rms to create RF arcing. The arcing causes cell destruction in the path of an electrode. To the knowledge of the applicants, there are no known devices available at present which are designed for "dry" bipolar RF electrosurgical cutting. However, a crude arrangement is known for use in "wet-field" surgery, in which two electrodes are dragged over the tissue to be cut in the presence of an irrigation solution. The purpose of irrigation of the tissue is to reduce the electrical resistance between the electrodes when they are first applied to the tissue so that an arc can be initiated. The principal factor impeding development of bipolar technology is that it is very difficult to direct the arc, which occurs between the two active electrodes, onto the patient. It is far easier to make the patient the return path for the RF energy as in monopolar electrosurgery.

Monopolar electrosurgery has two distinct disadvantages. Firstly, having only one active electrode means that cautery is not nearly as effective as with bipolar electrosurgery. A typical cautery requirement is to seal a blood vessel, and since a bipolar electrode arrangement creates a current path across the two active electrodes, the blood vessel is cauterised side-to-side, thereby minimising damage to adjacent tissue. In contrast, monopolar cautery, due to the remote position of the return electrode in another part of the patient's body, results in current passing along the tissue planes, which creates more damage. The other disadvantage, which is perhaps more important, is the effect of the patient connection of the return electrode. A considerable proportion of the RF energy used in monopolar electrosurgery is dissipated in the patient's body. The maximum output of a monopolar electrosurgical unit is typically 300 watts, and up to 200 watts may be dissipated elsewhere in the body. This can cause significant internal heating and concerns have been expressed about possible consequences. Another effect of using patient connection is that the patient does not assume the return or neutral electrode potential. As a result of the significant voltage drop across the torso, earthed components connected to the patient can create a sufficiently large current to cause RF burns outside the operating site. The most common cause of burns outside the operating site is the resistance between the return electrode and the patient. When this resistance increases, the localised dissipation increases, thus causing burns.

It is also known to perform electrosurgical cutting by means of a hot wire tool. Specifically, a metallic wire loop is heated using a low frequency alternating current, and the cutting action is purely by heat. In U.S. Pat. No. 4,089,336, the metallic wire loop is replaced by a blade having a loop of material which has a negative temperature coefficient of resistance so that power dissipation is concentrated in that portion of the loop which is cooled by application to the tissue to be cut. Hot-wire devices are, however, limited in their cutting speed by the maximum heat that can be generated without significantly reducing the stability and strength of the heated element.

SUMMARY OF THE INVENTION

Electrosurgical cutting is becoming more commonly used due to its advantages in reducing blood loss from cut tissue and due to the increasing use of so-called "minimally invasive" surgery. In order to meet the demand for a more effective means of performing electrosurgery, the present invention provides, according to one of its aspects, apparatus for bipolar radio frequency electrosurgery comprising a radio frequency generator having first and second output terminals, and a cutting assembly which includes a support structure with at least two electrical supply conductors and, mounted at a distal end of the support structure, a tissue cutting head comprising an exposed length of electrically conducting material electrically connected between the two supply conductors, the material having a negative temperature coefficient (NTC) of resistance, and connection means for allowing radio frequency electrical power to be fed from the output terminals of the generator to the supply conductors of the cutting assembly thereby to heat the cutting head and to permit tissue cutting by RF electrosurgery action. According to another aspect of the invention, there is provided apparatus for bipolar radio frequency electrosurgery comprising a radio frequency generator having first and second output terminals, and a cauterising assembly which includes a support structure with at least two electrical supply conductors and, mounted at distal ends of the supply conductors, a pair of cauterising jaw electrodes electrically connected to the supply conductors and movable relative to each other so that when one electrode engages the other an electrical circuit is formed between the supply conductors, at least one of the electrodes being formed of an electrically conductive material having a negative temperature coefficient (NTC) of resistance, and connection means for allowing radio frequency electrical power to be fed from the output terminals of the generator to the supply conductors of the cauterising assembly thereby to heat the NTC material when, during cauterisation, radio frequency current passes between the electrodes.

The effect of using, for example, a loop of NTC material as an RF electrosurgery cutter element is that when an RF voltage is applied across the loop it heats up rapidly as its resistance decreases. A point is reached at which the loop temperature is so high that its electrical resistance is very low. If, now, the loop is applied to the tissue to be cut, the tissue is easily cut due to the high temperature. Very quickly, however, that part of the loop which is in contact with the tissue cools down. Due to the NTC characteristic of the loop this part of the loop increases in electrical resistance with the result that the RF voltage drop is considerably greater across the tissue contact region than in other parts of the cutter element. If, then, the resistance of the cutter element is comparable to the electrical resistance of the tissue in the tissue contact region, significant RF currents pass through the tissue, producing the required RF electrosurgical action. This effect may be likened to an internal arc whereby the tissue impedance presents the path of least resistance between two hot, low resistance ends of the NTC cutter element on either side of the tissue contact region. In this way, the problem of directing the arc onto the patient associated with conventional bipolar devices is avoided. Also largely avoided is the tendency with prior bipolar devices to create two arc sites at the ends of the respective electrodes by virtue of the current path being from one electrode through the tissue path of least resistance, and then back from the tissue to the other electrode. In addition, it is possible to overcome the difficulty of the distances between tissue and electrodes being critical in determining cutting performance in prior bipolar cutting devices.

The NTC material used for the cutter element or electrodes may be selected from a wide range of compounds depending on the requirements to be met in the particular embodiments of the invention. When mechanical strength is required, for withstanding the mechanical resistance to cutting of tissue, a ceramic material such as silicon carbide, boron carbide, boron nitride, or zirconia is preferred. There exist, in addition, a number of suitable silica-based compounds as well as more complex glass ceramics using, for example, dopants for tailoring their electrical behaviour. Where mechanical strength is not so important, the semiconducting elements such as silicon or germanium may be used. Other factors determining the selection of the material are the ability to withstand thermal stress due to extremes of temperature, and the thermal coefficient of expansion (where matching to the coefficient of expansion of another material is required). Clearly, the material must also be non-toxic under the harsh conditions of use. In preferred embodiments of the invention described below, the cutter element and electrodes are made from sintered or reaction-bonded silicon carbide. Other materials having a much greater or much smaller range of resistivity variation over a temperature range of, say, 100° C. to 700° C. may be used, but materials in which the range is within a factor of 10 of 1K $\Omega$cm are preferred.

A further criterion in the choice of material is its resistivity. Glass ceramics have a wide range of resistivities, ranging from $10^2$ $\Omega$cm to $10^{18}$ $\Omega$cm at room temperature. Materials with a low resistivity may be used when cutting purely by the action of heat is sufficient, since then high power dissipation will occur at a low supply voltage level. Where electrosurgical RF currents are to be induced, with an RF voltage supply connected to the cutting tool, the resistance of the operating portion of the cutter element (or electrode pair when brought together) should be of a similar magnitude to the resistance of the surrounding tissue during the cutting operation so that some, if not most of the RF current passes from the cutter to the tissue. Thus, typically, the operating portion of the cutter element or electrodes should have a resistivity in the range of from 100 $\Omega$cm to 10 k$\Omega$cm at an operating temperature in the region of 70° C. to 130° C., and preferably at 100° C. Under these conditions, the cutting action is by both heat and RF electrosurgical action.

A particularly advantageous construction of the cutter element or electrodes makes use of metallic links joined to the NTC material for coupling the material to the supply conductors, the metallic links being made of a material having a thermal coefficient of expansion which at least approximately matches that of the NTC material. Preferably, each metallic link has an end portion which is embedded in the cutter element or electrodes. Thus, for example, tungsten links may be embedded in reaction bonded silicon carbide material.

The output impedance of the RF generator should at least approximately match the impedance of the cutter element in the operating condition, i.e. when an operating portion of the element is at a temperature of about 100° C. and the portions on either side of the operating portion are at a significantly higher temperature. When the cutter element is not in physical contact with any tissue or other material and power is applied to the element, its temperature can rise to very high levels so that its impedance is very low. To avoid too high a temperature being reached, with the possibility of damaging the NTC material, this decrease in impedance can be used to limit the RF power applied to the element. Thus, the RF generator may be so arranged with an output impedance which is completely mismatched to the low impedance of the high temperature cutting element. A more sophisticated approach is to tailor the generator performance such that below an impedance threshold, output power is shut down. Thus, the activated but non-applied state of the cutter element is made stable to prevent burn out of the NTC material. In the case of a RF power generator designed to operate at an output frequency which varies with load resistance in order to match the output impedance to the load resistance, as described in published British Patent Application No. 2214430A, the generator may incorporate a power reduction circuit which operates in response to output frequency in order to limit or switch off the output power when the cutter element is not in contact with the tissue. A further advantage of using a generator with an automatically variable output impedance is the ability to deliver significant power to the cutter element when it is in its cold, high resistance state to initiate heating of the element. The subject matter of the above-mentioned Application No. 2214430A is incorporated in this specification by reference.

One of the preferred forms of cutter element comprises a length of NTC material such as a glass ceramic formed into a loop, each end of the loop being coupled to a respective supply conductor in a handle of the cutting tool. Such a loop can be made very small (e.g. 2 mm or less in width and/or depth).

In another embodiment, the cutter element is formed as part of a rod having one end mounted to a handle, the rod having a coaxial sandwich structure. The innermost component of the structure is an axial support core which is preferably made of a metal such as steel or, when particularly high temperature resistance is required, tungsten. This inner core is coated in an electrically insulating material such as a non-conductive glass ceramic, and subsequently coated in an NTC material. At the distal end of the rod, the NTC material coating may be connected to the inner core, while at the proximal end, the core is connected to one supply conductor and the NTC material coating is connected to another supply conductor, so that the outer coating forms part of an electrical circuit between the two supply conductors. Alternatively the NTC coating may be left disconnected from the core at the distal end, the circuit being completed instead by living tissue when the tool is used.

To achieve maximum energy transfer by cooling of the whole circumference of the NTC material when in contact with tissue, the diameter of the rod is preferably less than 0.5 mm. This embodiment is particularly suitable for detailed cutting work and cutting can be omnidirectional.

Another embodiment of the invention takes the form of a pair of forceps having arms constituting or including respective electrical conductors and, secured to the distal end of each arm, a respective elongate electrode at least an operative portion of which is formed from an electrically conductive material having a negative temperature coefficient (NTC) of electrical resistance, the electrodes being so oriented on the arms that they may be brought into tip-to-tip contact by moving the arms towards each other to complete an electrical circuit between the supply conductors. Such a tool is useful for both cautery and cutting. Cautery is performed in a conventional manner, while for cutting the electrodes are brought together to form a loop and then brought into contact with the tissue. This has a secondary benefit compared with conventional bipolar electrosurgical cauterising tools in that the cauterised material which normally sticks to the tips of the forceps and impairs their performance can be burned off as soon as the electrodes are removed from the tissue since, then, the temperature of the NTC material rises to a high level, as described above, providing the electrodes are kept in the closed condition.

To avoid dissipation of heat to the handle or handles of the cutting tool, which, apart from being undesirable in itself, reduces the efficiency of the tool due to heat being conducted away from the cutter element, it is preferable to provide a thermal block or thermal resistance between the ends of the cutter element and the handle or handles. Accordingly, the supply conductors should have an adequate surface area of contact with the cutter element (or in the case of the forceps embodiment, with the electrodes), but proximally of those contacts, the conductors, together with any other support members, should have a relatively small cross section and may follow a convoluted path to reduce heat conduction.

The invention is applicable in general to a bipolar electrosurgical tool having a support structure with at least two electrical supply conductors incorporated in the structure and, mounted at the distal end or ends of the supply conductors at least one element for electrosurgical application to living tissue, the element forming, in use of the tool, part of an RF circuit between the supply conductors, and being formed of an electrically conductive material having a negative temperature coefficient of resistance and, preferably, an electrical resistivity which is in the same order as that of living tissue at 100° C.

BRIEF DESCRIPTION OF THE DRAWINGS

The invention will now be described by way of example with reference to the drawings in which:

FIGS. 1A to 1D are diagrams illustrating the principle of operation of a negative temperature coefficient cutting element using RF electrosurgery;

FIG. 2 is a longitudinally sectioned side view of part of a first surgical cutting tool in accordance with the invention;

FIGS. 2A, 2B and 2C are, respectively, a side elevation, a plan view, and a rear end elevation of an alternative cutting head;

FIG. 2D is a side elevation of a modified cutting head similar to that of FIGS. 2A to 2C;

FIG. 3 is a longitudinally sectioned side view of part of a second cutting tool in accordance with the invention;

FIG. 3A is a longitudinally sectioned side view of a further cutting head, similar to that of the cutting tool of FIG. 3;

FIG. 4 is a side elevation of a pair of cutting and coagulating bipolar forceps in accordance with the invention;

FIG. 4A is a side elevation of an electrode assembly of the forceps of FIG. 4;

DESCRIPTION OF PARTICULAR PREFERRED EMBODIMENTS

Figure 6:
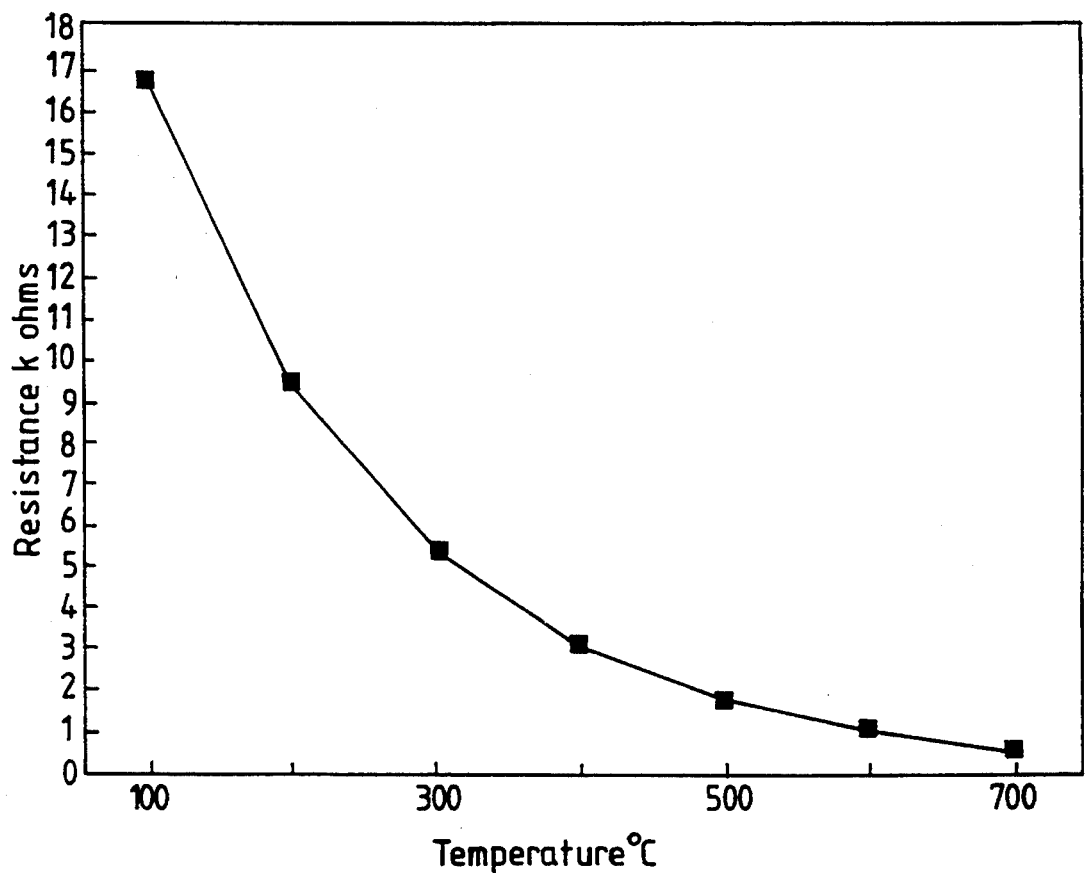
FIG. 6 is a graph of the resistance of a piece of a silicon carbide material plotted against temperature.

Referring to FIGS. 1A to 1D of the drawings, the principle of operation of an RF powered negative temperature coefficient cutting element is as follows. For the purposes of this explanation, consider a cutter element in the form of a straight bar of NTC material as shown in FIGS. 1A to 1C. In these figures, the temperature of the bar is shown by indicating cool regions as shaded and hot regions as white. Initially, when an RF voltage is first applied across the bar 10, as shown in FIG. 1A, its initial impedance is high (preferably greater than 20 k$\Omega$ and typically greater than 40 k$\Omega$) and, consequently, the potential drop across the bar is also high.

Providing the RF voltage is sufficient, the bar quickly heats up and reaches a temperature which is so high that its impedance is very low, as represented by FIG. 1B. The RF source may typically have an output impedance in the region of 5$\Omega$ to 100$\Omega$, which means that if the bar reaches a temperature of, say, 700° C. and the temperature coefficient of the material of the bar is such that its resistance drops to, say, 50$\Omega$, then the voltage across the bar drops significantly, as is shown by the graph part of FIG. 1B. In practice, the temperature of the bar when not in physical contact with anything can be between 200° C. and 1600° C. These temperatures are higher than when the cutter element is in contact with tissue since the latent heat of tissue water vaporisation causes the bar 10 to be cooled to a temperature which is normally not much in excess of 100° C. Thus, when not in contact with tissue, the resistance of the bar is at its lowest.

When the bar comes into contact with the tissue to be cut and begins to cut into it, as shown in FIG. 1C, the cutting region 10A of the bar is cooled, as just described, to a temperature in the region of 100° C. with the result that the resistance of that region of the bar is considerably higher than the regions outside the cutting region, and the major part of the potential drop across the bar is concentrated in the cutting region, as shown by the graph part of FIG. 1C. Providing, then, the resistance of the cutting region 10 is of a similar order to that of the tissue, RF currents pass from the bar to the tissue as shown in FIG. 1D. In addition, by arranging for the output impedance of the RF power source to match that of the bar in the operating condition, the maximum amount of power is transferred to the bar and, due to the potential drop characteristic produced by the NTC material shown in FIG. 1C, that power is concentrated in the cutting region, resulting in high cutting efficiency and comparatively little power dissipation in the regions outside the cutting region.

It should be noted that being able to heat the bar from cold depends on dissipating sufficient electrical power in the bar so as to exceed the heat dissipation. In practice, a power level of the order of 1 watt is sufficient, but an RF power generator capable of developing that level of power in a very high impedance load (typically 25 k$\Omega$ or greater) is needed in order to achieve the above described thermal runaway. An RF power source having an output impedance which is adjustable over a wide range, as described in British Patent Application No. 2214430A, is helpful in this respect.

In practice, the shape of the cutter element depends on the tasks to be performed. Referring to FIG. 2, a cutter assembly in accordance with the invention comprises a support structure 12 in the form of an insulation-sheathed stainless steel tube 12T forming one RF supply conductor and an insulated inner wire 12W forming a second RF supply conductor, and a cutting head 14 with a U-shaped cutting loop 14L made of silicon carbide NTC material and coupled to the supply conductors. The loop 14L is housed in a ceramic plug 14P fixed into the end of the tube 12T and has an exposed end projecting beyond the end of the plug 14P and two enclosed tails 14LT which have an aluminium coating. Inside the plug 14P the loop tails 14LT are received within and electrically connected to respective metallic connector sleeves 14S, one of which is bent over at its inner end inside the tube 12T and bonded to the inner surface of the tube. The other sleeve 14S also projects beyond the plug 14P inside the tube 12T and receives the exposed end of the inner wire 12W.

A degree of thermal isolation of the loop 14L from the tube 12T is provided by the length of the tails 14LT of the loop 14L and the connector sleeves 14S projecting beyond the end of the tube 12T inside the ceramic plug 14P.

The tube 12T may be part of a handle for the tool, or it may form the supporting shaft of a laparoscopic tool for so-called minimally invasive surgery. At its end remote from the cutting head 14 a connector (not shown) is provided for connection to the output terminals of an RF generator.

Referring to FIGS. 2A to 2C, as an alternative to the loop 14L of the embodiment of FIG. 2, the cutting head may include a shorter, generally U-shaped loop 16 of silicon carbide or glass ceramic bonded to a pair of metallic links 18 each of which has an end portion embedded in a respective tail of the loop. In a preferred construction, the loop is reaction bonded silicon carbide which has been moulded over the ends of two elongate tungsten links 18, tungsten having a thermal coefficient of expansion which closely matches that of silicon carbide to avoid breakdown of the joints between the links and the loop due to the large changes in temperature occurring during use.

The applicants have found that by applying an insulating glaze to the cutter loop 16, with the glaze being interrupted at intervals around the outermost surfaces of the loop, as shown by the apertures 20 in FIG. 2D, localised electric field concentrations are produced due to the reduction in the total area contact between the loop and the tissue. This means that a significant potential drop occurs between each exposed portion of the NTC material, thereby increasing the ability to produce arcing in the tissue adjacent each aperture in the glaze.

For fine cutting operations, a cutter head in the form of a rod 30 supported at only one of its ends is preferred, as shown in FIG. 3. In this embodiment, the cutter head is constituted by a coating 30C of silicon carbide material applied to an insulative ceramic tube 30T. Inside the tube 30T is a metallic rod 30R acting as an inner core. At the proximal end, the NTC coating 30C is fixed in a metal bush 32 forming part of a plug 34 inserted in the end of a steel tube 12T like the tube 12T of the embodiment of FIG. 2. Tube 12T forms one supply conductor which is connected to the NTC coating 30C by the bush 32. The inner rod 30R of the cutting head of this embodiment is coupled to an inner conductor wire 12W in the tube 12T, the cutter head 30 and the connection to the wire 12W being housed in the plug 34 which, on both sides of the bush 32, is made of an insulating ceramic material. In the embodiment of FIG. 3 there is no connection between the inner rod core 30B and the NTC coating 30C, the electrical circuit only being completed when the end of the cutter rod touches the tissue to be cut. When a distal end connection is required before contact with tissue, the silicon carbide of the outer coating 30C may be continued over the end of the ceramic tube 30T as an end cap 30D to make contact with the inner rod core 30R, as shown in FIG. 3A. In this figure, an alternative connector to the outer coating 30A is shown in the form of a platinum wire 30W wound around the coating at the proximal end thereof and secured in place by a bead 30B of ceramic glue.

The metallic core 30R is preferably sufficiently rigid to act as a support for the ceramic tube 30T and the NTC coating 30C, and may be made of tungsten or, if the maximum temperature of the rod 30 can be limited, steel. The ceramic tube 30T is preferably a non-conducting glass ceramic, while the NTC material may be silicon carbide or a conducting doped glass ceramic. It is important to ensure that both components of the rod 30 which are bonded together, particularly the NTC coating 30C and the insulating ceramic tube 30T, have closely matched thermal expansion coefficients to minimise the possibility of fracture.

It will be appreciated that the rods 30, as shown in FIGS. 3 and 3A, can be used for cutting in any direction, whereas the loops 14L and 16 of FIGS. 2A to 2D are used primarily for cutting in the plane of the loop.

A further embodiment of the invention is in the form of a surgical tool having two electrodes each mounted at the end of a respective one of a pair of arms or handles, as shown in FIG. 4. Referring to FIG. 4, a pair of forceps has two elongate silicon carbide electrodes 40 forming the tips of the arms 42 of the forceps, each arm constituting an electrical supply conductor connected, in operation, to respective terminals of an RF power generator. Those parts of the arms 42 which form the handles for the operator are insulated.

With reference to the detail drawing of FIG. 4A, each electrode 40 is moulded onto a comparatively thin tungsten rod 44 which is, in turn, integral with a metallic connector 46 having a recess 46A shaped to receive the metallic body of the respective forcep arm 42 forming the supply conductor. Each electrode 40 is tapered and is oriented with respect to the metallic connector 46 such that when the arms 42 are squeezed together, the tips of the electrodes 40 touch so as to form an electrical circuit between the supply conductors. In the manner described hereinbefore, application of an RF voltage to the supply conductors when the electrodes are touching causes rapid heating of the electrodes and a consequent increase in their temperature. When, however, the electrodes come into contact with tissue to be cut, a localised drop in temperature occurs thereby concentrating the voltage drop to the cooled region with the effect of cutting the tissue by an RF electrosurgical action as described above.

The tungsten links 44 between the electrodes 40 and the connectors 46 are of comparatively small cross section in order to reduce heat conduction to the arms 42. Tungsten is chosen as a material for the links 44 because, firstly, it has a thermal coefficient of expansion which is very close to that of silicon carbide, and secondly it is capable of withstanding very high temperatures.

Repeated use of the forceps described above produces wear at the tips of the electrodes 40 due to arcing between the tips when the forceps are opened after having heated up. This arc is developed because hot ionised air is produced around the tips. The wear rate can be significantly improved by modulating the applied RF waveform with the result that any ionised air will only be produced for the short duration of one modulation cycle. If the average RF power dissipation is maintained at the same level as for a continuous sine wave, the peak voltages across the operating portion of the electrodes when brought together by closing the forceps are higher, thereby increasing the RF electrosurgical cutting action. It will be appreciated that modulating the RF supply in this way is also advantageous for the other surgical tool embodiments described above due to the increased electrosurgical action.

Figure 5:
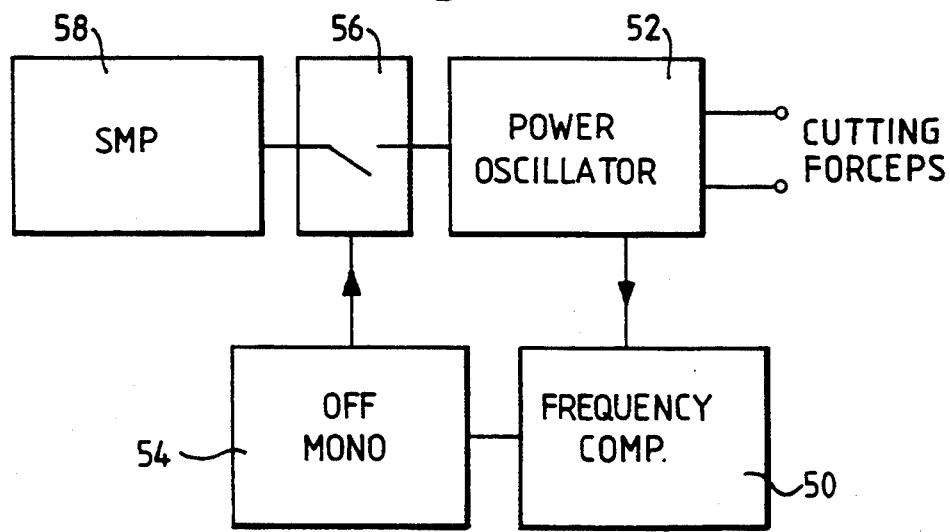
FIG. 5 is a simplified block diagram of an RF power source.

The above-mentioned published Application No. 2214430A discloses an RF generator having a power oscillator operable over a range of frequencies, the actual output frequency depending on the resistance of the load presented to the generator. This characteristic of the generator may be made use of in providing an automatic shut-down facility for limiting the temperature of the cutting element or electrodes when not actually in contact with tissue. Referring to FIG. 5, a suitable RF generator has a frequency comparator 50 coupled to receive a signal representative of the output of the power oscillator 52. The comparator 50 is arranged such that when the sensed carrier frequency drops below a predetermined frequency threshold, a monostable circuit 54 is triggered which, in turn, causes a switching device 56 to be operated so as, in this embodiment, to remove power from the power oscillator. In this example, this is achieved simply by breaking the circuit between a switched mode power supply 58 and the oscillator 52. Other means of reducing or shutting off the oscillator output can be used. The monostable circuit 54 holds the switching device 56 in the "off" state for a predetermined time at the end of which the power oscillator is restarted. If then it settles at a frequency which is still below the frequency threshold, the monostable circuit 54 operates once again. Thus, since the output frequency of the oscillator varies with the magnitude of the load impedance (the frequency increasing with increasing impedance), it is possible to maintain the oscillator in a reduced power or deactivated condition when the cutting element or electrodes have reached a predetermined upper temperature limit, thereby avoiding damage due to burning.

With regard to the conditions for optimum RF electrosurgical cutting, it has been found that the increased electrosurgical action obtainable using a modulated RF power signal allows quite a wide range of NTC material resistivities to be used. Experience has shown that the most useful range is between 100 Ωcm and 10 kΩcm at 100° C. The resistivity and the nature of the applied waveform are interactive. A comparatively low resistivity requires high peak voltages for optimum RF electrosurgical action, which means that the practical limitation at the low resistivity end of the range is the ability to produce a modulation waveform with a significantly high crest factor (peak voltage to rms voltage ratio). At the high end of the resistivity range the extent to which current passes through the tissue acts as a limitation. It is not at first obvious that too much power could pass into the tissue. However, it should be appreciated that in a deep cutting operating too high a resistivity will result in most of the current passing from the cutter element or electrodes into the tissue so that, beyond a certain depth, there is insufficient power to provide the required potential drop at the surface of the NTC material to provide cutting action. High resistivity therefore limits the depth of cut but provides the highest degree of RF electrosurgical action.

As an illustration of the range of resistance obtainable using negative temperature coefficient materials, FIG. 6 shows the resistance of a rod of silicon carbide material having the dimensions 25 mm×1 mm×1 mm over the temperature range 100° C. to 700° C. It will be seen that over this temperature range, the resistance changes by a factor of at least 20. The resistivity of silicon carbide at room temperature is in the range of from 1 kΩcm to 1M Ωcm, depending on the form in which it is used.

We claim:

1. Apparatus for radio frequency (RF) bipolar electrosurgery comprising a radio frequency generator having first and second output terminals, and a cutting assembly which includes a support structure with at least two electrical supply conductors and, mounted at a distal end of the support structure, a tissue cutting head comprising an exposed length of electrically conducting material electrically connected between the two supply conductors, the material having a negative temperature coefficient (NTC) of resistance, and connection means for allowing RF electrical power to be fed from the output terminals of the generator to the supply conductors of the cutting assembly thereby to heat the cutting head and to permit tissue cutting by RF electrosurgical action.

2. Apparatus according to claim 1, wherein the cutting head is formed as a loop of the NTC material.

3. Apparatus according to claim 1, wherein the cutting head includes metallic links having end portions embedded in respective ends of the length of NTC material for connecting the latter to the supply conductors.

4. Apparatus according to claim 3, wherein the NTC material is reaction-bonded silicon carbide and the links are formed of tungsten.

5. Apparatus according to claim 3, wherein the NTC material is silica-based.

6. Apparatus according to claim 1, wherein the cutting head includes metallic links joined to each end of the length of NTC material for connecting the latter to the supply conductors, and wherein the NTC material is silicon carbide and the metallic links are formed of tungsten.

7. Apparatus according to claim 1, wherein the NTC material has resistivity in the range of from 100 Ωcm to 10 kΩcm at 100° C.

8. Apparatus according to claim 1, wherein the resistance of the cutting head at 25° C. is greater than 20 kΩ.

9. Apparatus according to claim 8, wherein the resistance of the cutting head at 25° C. is greater than 40 kΩ.

10. Apparatus according to claim 1, wherein the generator operating frequency is greater than 300 kHz and produces an output voltage when in use in excess of 50 Vr.m.s.

11. Apparatus according to claim 1, wherein the RF generator has a configuration such that when the resistance of the cutting head falls below a predetermined threshold, the output power of the generator is limited to set an upper temperature limit for the NTC material.

12. Apparatus according to claim 11, wherein the RF generator has an output impedance and output frequency which vary automatically according to the resistance of the cutting head, the generator including means for monitoring the output frequency and operable to reduce the output power of the generator from a set level when the output frequency crosses a predetermined frequency threshold indicative of the temperature of the cutting head having risen to an upper temperature limit.

13. Apparatus according to claim 12, wherein the RF generator includes a timing circuit operable, after the reduction in output power, to cause the generator to re-apply output power at the set level after a predetermined time interval, to monitor the output frequency again, and to cause the output power of the generator to be reduced again if the frequency is indicative of the cutting head temperature being still too high.

14. Apparatus for radio frequency (RF) bipolar electrosurgery comprising a radio frequency generator having first and second output terminals, and a surgical instrument which includes a support structure with at least two electrical supply conductors and, mounted at a distal end of the support structure, a tissue treatment head comprising an exposed length of electrically conducting material electrically connected between the two supply conductors, the material having a negative temperature coefficient (NTC) of resistance, and connection means for allowing RF electrical power to be fed from the output terminals of the generator to the supply conductors of the instrument thereby to heat the treatment head and to permit tissue treatment by RF electrosurgical action.

* * * * *